United States Patent [19]

Hahn

[11] Patent Number: 5,194,637

[45] Date of Patent: Mar. 16, 1993

[54] METHOD AND APPARATUS FOR SYNTHESIS OF HIGHLY ISOMERICALLY PURE STEREOISOMERS OF GLYCIDOL DERIVATIVES

[75] Inventor: Roger C. Hahn, Syracuse, N.Y.

[73] Assignee: Syracuse University, Syracuse, N.Y.

[21] Appl. No.: 748,672

[22] Filed: Aug. 22, 1991

[51] Int. Cl.$^5$ ................. C07D 301/00; C07D 301/32
[52] U.S. Cl. .................... 549/559; 549/345; 549/427; 549/497; 549/510; 549/511; 558/51
[58] Field of Search ............... 549/556, 345, 427, 497, 549/510, 511; 558/51

[56] References Cited

U.S. PATENT DOCUMENTS

| | | | |
|---|---|---|---|
| 3,053,855 | 9/1962 | Maerker et al. | 260/348 |
| 3,859,314 | 1/1975 | Dukes et al. | 260/348.6 |
| 4,395,542 | 7/1983 | Sury | 528/481 |
| 4,540,769 | 9/1985 | Dobinson et al. | 528/90 |
| 4,810,808 | 3/1989 | Tomita et al. | 549/515 |
| 4,831,101 | 5/1989 | Jellinek et al. | 528/87 |
| 4,931,576 | 6/1990 | Wirth et al. | 549/514 |

OTHER PUBLICATIONS

Advertisement, Aldrich Chemical Co. *J. Org. Chem.*, vol. 55, #19 (1990).
Aitken, Royer, and Husson, *J. Org. Chem.* 55:2814-2820 (1990).
Guivisdalsky, and Bittman, *J. Org. Chem.* 54:4643-4648 (1989).
Byun, and Bittman, *Tetrahedron Letters*, vol. 30, #21:2751-2754 (1989).
Hahn and Tompkins, *J. Org. Chem.* 53:5783-5785 (1988).
Klunder, Tetsue and Sharpless, *J. Org. Chem.* 54:1295-1304 (1989).
Nitta, Arakawa and Naoto, *Chem. Pharm. Bull.* 34:2710 (1986).
Najdi, Reichlin and Kurth, *J. Org. Chem.* 55:6241-6244 (1989).
Jurczak, Pikul, and Bauer, T. *Tetrahedron* 42,2:447-450.

*Primary Examiner*—Joseph E. Evans
*Attorney, Agent, or Firm*—Wall and Roehrig

[57] ABSTRACT

Methods are provided for producing isomerically enriched camphorsulfonates, and in particular a diastereomerically enriched glycidyl camphorsulfonate by bromide-casylate exchange between an alkyl casylate and the bromide analog of the desired casylate, followed by separation of a higher melting diastereomer by selective recrystallization. There is also shown the production of a desired casylate by reacting a racemic or enantiomerically enriched arenesulfonate with a quaternary casylate. Randomization and recycling of an isomerically enriched casylate is provided by reaction with an achiral bromide analog in the presence of a quaternary salt. Specially adapted apparatus for conducting the randomization reaction is provided. There is also shown a process for producing an alkyl casylate by the reaction of a metal casylate and a quaternary casylate with a trialkyl phosphite in the presence of a slight molar excess of sulfuric acid.

5 Claims, 3 Drawing Sheets

METHOD AND APPARATUS FOR SYNTHESIS OF HIGHLY ISOMERICALLY PURE STEREOISOMERS OF GLYCIDOL DERIVATIVES

BACKGROUND OF THE INVENTION

This invention relates to highly isomerically pure stereoisomers of glycidol derivatives, and more particularly to the preparation of highly purified diastereomers of glycidyl camphorsulfonate.

Stereoisomers of glycidol, having the formula (1) and certain of their derivatives are important intermediate compounds for asymmetric synthesis in various commercially important fields. They have been used to prepare pharmaceuticals such as antibacterial agents and β-blockers, Other uses include the preparation of pheromones, useful phospholipids, and other biologically active substances.

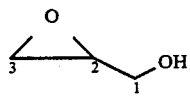
(1)

Glycidol itself is relatively unstable and water soluble, rendering its preparation technically demanding. It is produced by a potentially hazardous peroxide oxidation process, and is a suspected carcinogen. It is commercially available in optical purity of 88–90%.

In U.S. Pat. No. 4,831,101 to Jellinek et al it is shown that polyglycidyl ethers can be prepared by reacting a member of the group consisting of mono- and polyvalent phenols, aromatic amines, and aromatic carboxylic acids with an epihalohydrin. U.S. Pat. No. 4,810,808 to Tomita et al discloses another process for preparing a polyglycidyl compound in which an aromatic hydroxycarboxylic acid having a phenolic hydroxyl group is reacted with an epihalohydrin in the presence of a phase transfer catalyst, followed by dehydrohalogenation.

In U.S. Pat. No. 4,931,576 to Wirth et al there is disclosed a process for producing a glycidyl thioether by reacting a mercaptan with epichlorohydrin.

U.S. Pat. No. 3,053,855 to Maerker et al discloses that glycidyl esters can be prepared by reacting epichlorohydrin with an aqueous solution of an alkali metal salt of an organic carboxylic acid in the presence of a quaternary ammonium halide.

The processes disclosed in the above noted patents are not directed to the production of optical isomers of the glycidyl derivatives.

The production of optical isomers of glycidol derivatives is known. Certain arenesulfonate derivatives of partially purified glycidol can be crystallized to higher optical purity, but only at significant losses of product. 2,3-Isopropylideneglyceraldehyde having the formula (2) can be obtained as pure optical isomer from D-mannitol or ascorbic acid by processes involving oxidation. However the oxidants, which include lead tetraacetate and sodium periodate, are expensive and environmentally unattractive. Also, 2,3-Isopropylideneglyceraldehyde is sensitive to acid or base-catalyzed racemization, and is difficult to store. It is not commercially available.

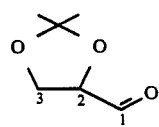
(2)

Another glycidol derivative, epichlorohydrin, having the formula (3) is obtainable commercially as either pure optical isomer. It may be produced by an enzymatic resolution process, but is quite expensive.

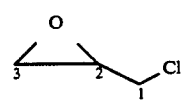
(3)

Furthermore epichlorohydrin is volatile, highly toxic, and a suspected carcinogen.

Still another compound, benzyl glycidyl ether, having the formula (4), is commercially available as either optical isomer. The optical purity can be as low as 76%, and the compound also is rather expensive.

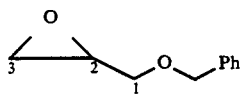
(4)

The preeminent preparative methodology currently used to prepare glycidol derivatives is either enzymatic resolution or Sharpless Asymmetric Epoxidation. As aforementioned, these methods present problems of incomplete optical purity, long, expensive, and hazardous synthesis routes, and handling and storage instabilities.

SUMMARY OF THE INVENTION

It is therefore a primary object of the present invention to economically prepare stereoisomers of glycidol derivatives which have superior optical purity.

It is another object of the invention to increase safety in the production of glycidol derivatives.

It is still another object of the invention to produce glycidol derivatives using materials that are relatively stable and easily handled.

It is explained in Hahn, R. C.; Tompkins, J. *J. Org. Chem.* 1988, 53: 5783 that alkyl halides can be converted directly to sulfonates by catalyzed homogeneous nucleophile exchange. It is also known that some optically active glycidol derivatives, in particular enantiomerically enriched glycidyl arenesulfonates are crystalline solids and that melting point differences between an enantiomer and a racemic mixture sometimes can be exploited in purifying glycidol derivatives by crystallization. Those desiring additional information about the characteristics of optically enriched glycidyl arenesulfonates are referred to Sharpless, K. B. et al, *J. Am Chem. Soc.* 1987, 109:5765,; Klunder, J. M.; Onami, T.; Sharpless, K. B. et al, *J. Org. Chem.* 1989, 54:1295; and Klunder, J. M.; Ko, S. Y.; Sharpless, K. B. *J. Org. Chem.* 986. 51:3710.

It was discovered by the inventor that epibromohydrin can be converted to a novel compound, glycidyl camphorsulfonate, the stereoisomers of which have the formulas 5(a)–5(d), and that the enantiomers of one diastereomer of glycidyl camphorsulfonate, Epi,OCas$_S$ or Epi$_S$OCas$_r$ each can be selectively crystallized from a mixture of stereoisomers. It is a further feature of the invention that mother liquors from crystallization of such a diastereomer may be conveniently randomized and subjected to another selective crystallization, thereby creating a recycling procedure for the epoxide moiety. The methodology also includes a recycling procedure for the casylate moiety, so that the invention may be practiced with great economy. All of the isomers of glycidyl camphorsulfonate, at any level of isomeric purity, are non-volatile, and are at least as stable as any previously reported derivative of glycidol known to the inventor. After more than a year samples unprotected from air, light and moisture show no sign of degradation. The processes and apparatus described herein are suitable for producing a wide variety of glycidol derivatives.

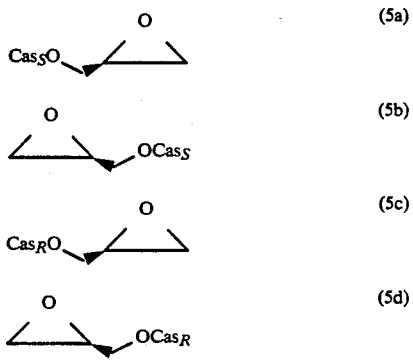

The above objects and other objects and advantages of the present invention are attained by several related processes and specially adapted apparatus as will become apparent from the following detailed description of the invention.

BRIEF DESCRIPTION OF THE DRAWINGS

For a better understanding of these and other objects of the present invention, reference is made to the detailed description of the invention which is to be read in conjunction with the following drawings, wherein.

DETAILED DESCRIPTION OF THE INVENTION

Figure 2:
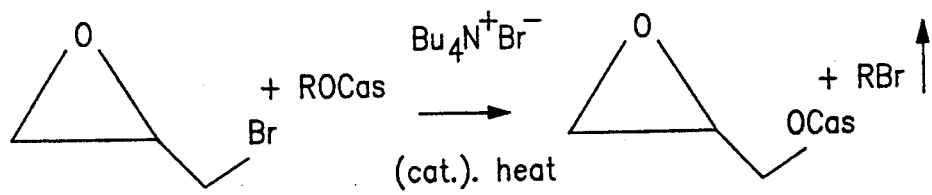
FIGS. 2-6 represent chemical reactions that are helpful in understanding the invention.

Process A:

Step 1, Preparation of crude glycidyl casylate: In the preferred embodiment of the invention, glycidyl casylate is prepared by a reaction in accordance with FIG. 2. The starting materials are racemic epibromohydrin, 1.5 to 3.0 equivalents, 1.0 equivalents of an alkyl camphorsulfonate (hereinafter referred to as casylate), and a quaternary salt catalyst, which can be an ammonium or phosphonium salt, but is preferably tetrabutylammonium bromide or casylate, 1.0 mole per cent of total ingredients.

Figure 3:
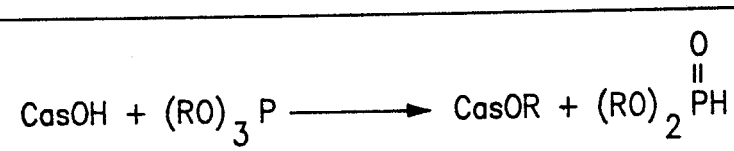

The alkyl casylate may be prepared in one step from either enantiomer of camphorsulfonic acid by a reaction in accordance with FIG. 3. The procedure is based on a known process, which has been improved by performing the reaction without a solvent, and by shortening the reaction time. To a thoroughly dried amount of the camphorsulfonic acid is added 1.0 or more molar equivalents of a trialkyl phosphite, preferably triethyl phosphite (slight exotherm). The mixture then is heated to about 80 degrees C. for 15 minutes or until analysis (most conveniently $^1$H NMR) indicates the absence of camphorsulfonic acid. Removal of all phosphorus-containing species by careful distillation at reduced pressure leaves a high yield of quite pure alkyl casylate. Alternatively, the alkyl casylate may be advantageously produced by recycling via Process C, discussed below. The alkyl casylate is preferably ethyl; however other alkyl casylates such as methyl or n-propyl casylate may be utilized.

The above described starting materials are mixed together in a pre-dried flask fitted with a gas bubbler, such as $N_2$ gas, an internal thermometer, and a takeoff condenser set on a vigreux column. With gentle gas purging, the mixture is heated to an internal temperature of 115°-125° C. RBr distills out. Residual water in the system, which appears to impede the exchange process, also azeotropes out. The reaction progress is conveniently monitored by $^1$H NMR spectroscopy. After about 3-5 hours at 115°-125° C., part of the original epibromohydrin is converted to a 1:1 mixture of diastereomers of glycidyl casylate, and the alkyl casylate is about 98% converted to alkyl bromide. The gas purge is important to remove the latter, and thus facilitate driving the reaction to completion. The catalyst now is nearly all in the form of tetrabutylammonium casylate ($Bu_4N^+OCas^-$). The calculated yield of glycidyl casylate takes this into account. Temperatures significantly higher than 125° C. may result in some darkening of the reaction mixture, which normally is pale tan, the color also depending on the purity of the starting materials.

The reaction may be conducted by adding epibromohydrin as the reaction proceeds, allowing a smaller reaction vessel to be used and reducing the amount of catalyst required.

To isolate crude glycidyl casylate, excess epibromohydrin is distilled out at reduced pressure (kugelrohr, 50-100 mm Hg, oven temperature 70°-90° C.). Recovery of epibromohydrin is nearly quantitative; its removal must be essentially complete to achieve optimal results in subsequent processing. The viscous residue consists almost entirely of $Bu_4N^+OCas^-$ and glycidyl casylate, with a yield of the latter exceeding 95%.

Because the above process is thermoneutral, it can be scaled up with no temperature control problems, although care should be taken to prevent the presence of acids, bases, or other substances which might initiate epoxide ring opening or polymerization. Because no solvent is used, a multi-mole scale reaction can be performed in readily available vessels having capacities of 22 liters or more.

It is also possible to prepare glycidyl casylate by a type of reaction known to the art, namely the reaction of commercially available glycidol with either enantiomer of camphorsulfonyl chloride. Racemic and approximately 90% optically pure glycidol both are commercially available from ARCO and from Aldrich Chemical Co. While the yields from this reaction are excellent, it is believed to be inferior to Process A because of the relative instability of glycidol, as compared with epibromohydrin, and the labor and unpleasantness involved in preparing and handling large amounts of camphorsulfonyl chloride. Also a much larger volume of solvent is needed for comparable amounts of reactants, and the subsequent workup is more laborious than in Process A.

Step 2, purification of one glycidyl casylate diastereomer. The crude 1:1 mixture of diastereomers of glycidyl casylate, free of epibromohydrin, is dissolved in methanol, 2.5:1 V/W solvent/solute. This is done without heating in order to minimize epoxide ring opening, as solutions in methanol at about 20° C. can undergo approximately 2% ring opening per day. The methanolic solution is rapidly cooled to 1°–3° C., and seeded with crystals of the pure (>98% de) higher-melting diastereomer (mp 60°–61° C.) with no stirring, and carefully observed as chunky, transparent crystals form. After about one hour, the temperature is gradually lowered to as low as −5° C. or lower, with continued observation. After the earlier of a total of three hours from seeding, or when formation of a fanshaped, rapidly growing crystal begins, the mother liquor is rapidly and thoroughly suctioned off, and immediately stripped of solvent. The fan-shaped crystal has a strong exotherm schlieren that is visible under suitable lighting, and is different from the preceding crystal form. The mother liquor has a diastereomeric composition of about 40:60 to 35:65 in favor of the lower-melting stereoisomer. The first crystal crop, about 70:30 to 80:20 in favor of the higher-melting stereoisomer by NMR assay, is recrystallized three more times in methanol, 3:1 V/W, with seeding at progressively higher temperatures, cooling to 0° C. The recrystallizations are not attended by the appearance of a second crystalline form, and give consecutive crops having approximate respective compositions of 93:7, 97:3, and 99:1 in favor of the higher-melting diastereomer. The three mother liquors that result from the latter three recrystallizations, stripped of solvent, are enriched in the higher-melting diastereomer, and are advantageously added at appropriate stages to a subsequent batch of glycidyl casylate which is undergoing recrystallizations. NMR assays of the mother liquors, combined with knowledge of crop weights, enables calculation of crop purities beyond the normal limits of NMR methodology. The final crop from the first batch represents up to about 35% of the initially available amount of the higher-melting diastereomer, and has $[\alpha]_D \pm 25.8°$ (c 10, CHCl$_3$).

Although Process A has been explained with reference to glycidyl casylate and epibromohydrin, it is applicable to preparation of casylates having formula (11), wherein R$_1$, R$_2$, and R$_3$ are bromide, bromomethyl, alkyl, or hydrogen, provided that R$_1$, R$_2$, and R$_3$ are each different. Process A is also applicable to preparation of casylates having formulas (12) or (13),

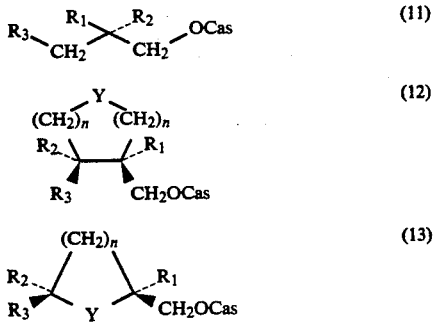

wherein R$_1$, R$_2$, and R$_3$ independently of one another are bromomethyl, alkyl, or hydrogen, n is 0, 1, or 2, and Y is oxygen, C=O, or —CH$_2$—. To prepare the foregoing compounds, Process A is conducted by reacting at least 1.0 equivalents of a racemic or achiral bromide analog thereof with an alkyl casylate.

In a preferred embodiment Process A is readily applied to preparation f glycidyl camphorsulfonates of formula (8a) or (8b), wherein R$_1$, R$_2$, and R$_3$ independently of one another are bromomethyl, methyl, ethyl, or hydrogen.

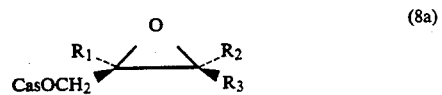

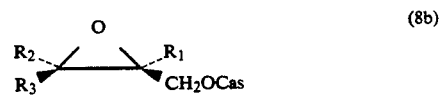

Figure 1:
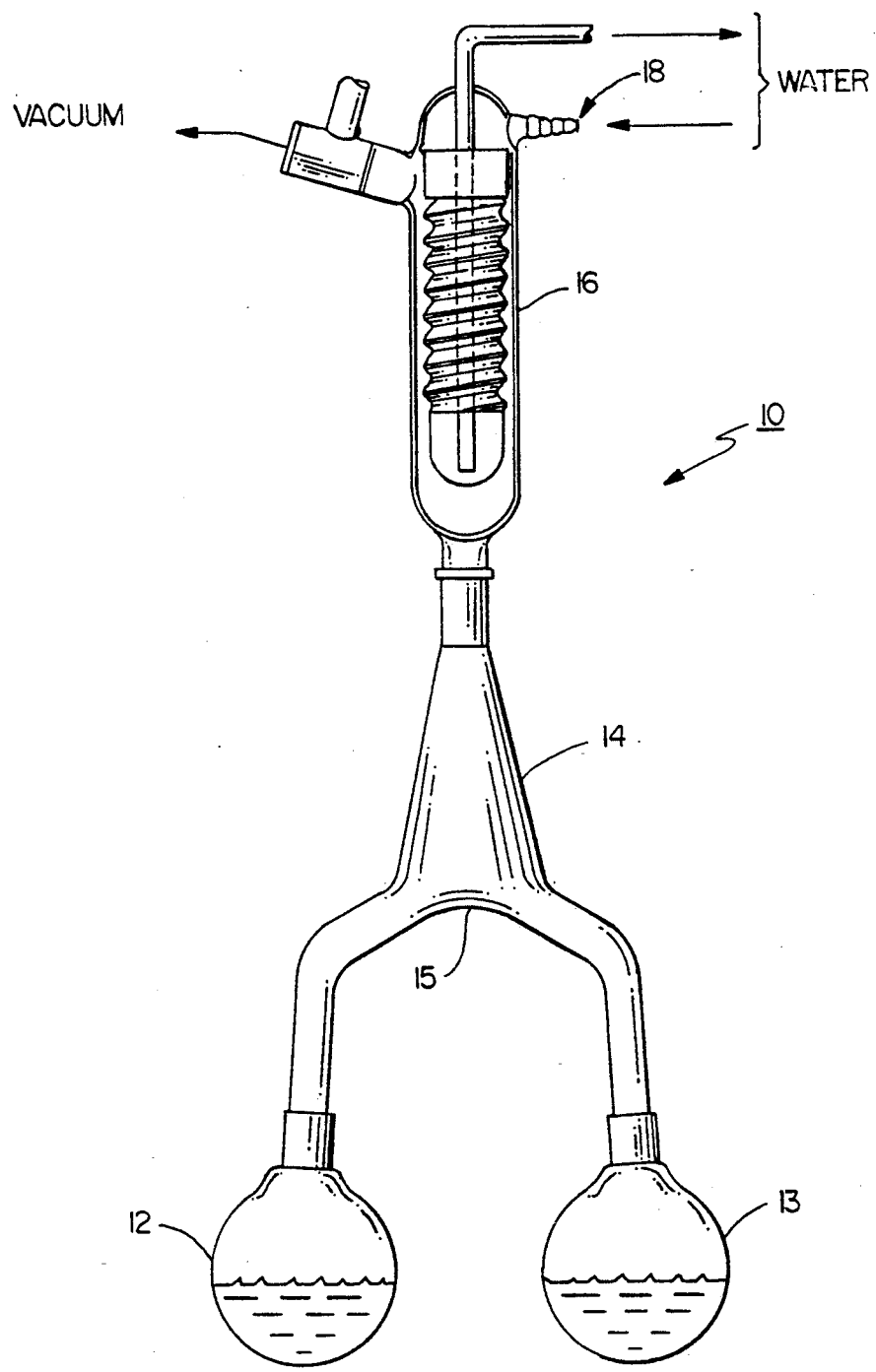
FIG. 1 is a side elevation of an apparatus that is useful in carrying out the invention.

Process B and B*: Randomization and recycling of glycidyl derivatives. Although the more general Process B is applicable to any camphorsulfonates which undergo quaternary salt-catalyzed bromide-casylate exchange, it is explained here with reference to glycidyl casylate and epibromohydrin. The reaction is conducted with two distinct mixtures in specially adapted apparatus. Turning now to FIG. 1, there is shown generally at 10 an apparatus for performing Process B. Two reaction vessels 12, 13 are charged with equivalent amounts of two glycidyl casylate crystallization mother liquors from enantiomeric casylates, from which solvent has been stripped. They may contain quaternary salt from Process A. Each liquor is mixed with up to 1 equivalent of racemic epibromohydrin, and exchange catalyst is added, if necessary, to bring its concentration to 2 mole % or higher. Tetrabutylammonium bromide or the appropriate enantiomer of tetrabutylammonium casylate can be used in this reaction.

Figure 4:
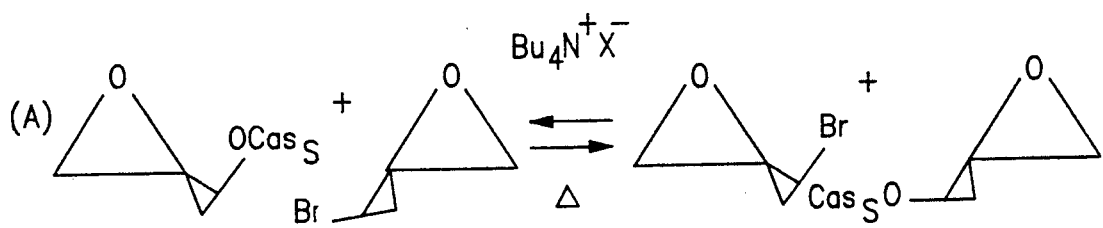
Figure 4:
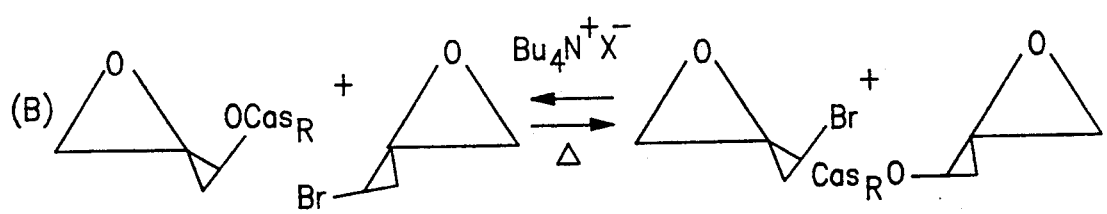

Each vessel is connected in sealing contact with a connecting member 14 that is disposed above the vessels. The connecting member 14 is adapted to sealably connect with reflux condenser 16, the condenser having a port 17 that receives a vacuum line (not shown) and ports 18, 18 for cool water lines (not shown). Epibromohydrin vapors rising from the reaction vessels circulate freely within the system, mix in the connecting member, and return to a liquid phase in the reflux condenser. It is preferable that the floor or bifurcation 15 in the lower portion of member 14 be convex, so that the condensate flows back into the reaction vessels without pooling in the connecting member. In conducting the reaction, each vessel is heated to 115°–125° C. until epibromohydrin begins to reflux. The temperatures of the boiling, equilibrating mixtures are controlled by composition and pressure, the latter being more conveniently varied than the former. The liquid levels in the two vessels preferably are maintained constant throughout the randomization; they can be controlled by adjusting the heat input to each vessel, adjusting the amount of insulation outside the conduits between each vessel and connecting member 14, adjusting the bifurcation of condensate backflow into the two vessels, or any combination of said adjustments. Raising the percentage of epibromohydrin in a vessel lowers the pot temperature in that vessel. Lower internal temperatures result in slower equilibration; higher temperatures may cause slow mixture decomposition. Although some tan color may develop during this process, this can be minimized by using purified mixture components. Heating is maintained until analysis by some suitable means such as $^1$H NMR indicates that the glycidyl casylates in each vessel are acceptably randomized. Two to three hours suffice to reach diastereomer compositions of 52:48 or better. In this system the initial casylate diastereomeric bias or excess in one vessel is balanced by a mirror image bias in the other, and as biased epibromohydrin is generated, its ability to circulate between vessels facilitates equilibration through the leveling of all biases. The processes that occur in the two vessels are shown in FIG. 4, wherein X is Br or OCas. At equilibrium, each vessel contains racemic epibromohydrin and a 50:50 mixture of diastereomers of glycidyl casylate. The glycidyl casylate may then be processed as explained above in Process A and Step 2 thereof.

Process B, as described above, is applicable to any camphorsulfonates, including glycidol derivatives, which undergo salt-catalyzed bromide-casylate exchange. Such compounds include those of formulas (5a–5d), (11)–(13), (8a), and (8b), shown above. For compounds which have a skeletal plane of symmetry in that part of the molecule attached to the camphorsulfonate moiety, a simpler Process B* suffices to afford randomization; Process B then is unnecessary. Such compounds include those of formula (11) when $R_3$ is bromide, [(12), (13), (8a), and (8b)] when $R_1=R_2$ and $R_3$ is bromomethyl, and [(12), (13), (8a), and (8b)] when $R_2=R_3$ and $R_1$ is bromomethyl.

In Process B*, a single reaction vessel, fitted the same as described in Process A, is charged with a casylate crystallization mother liquor from which solvent has been stripped. It may contain quaternary salt from Process A. Not less than three equivalents of the corresponding bromide are added, plus quaternary salt, if necessary, to bring its concentration to 2 mole % or higher. At this point, more randomized casylate also can be conveniently generated by adding additional corresponding bromide, plus an equivalent amount of alkyl casylate (preferably ethyl casylate). The entire mixture then is submitted to Process A.

It bears emphasizing that only Process B as described is a general randomization procedure, and that Process B* as described does not completely randomize casylates lacking a skeletal plane of symmetry, such as glycidyl casylate [formula (8a) where $R_1=R_2=R_3=$hydrogen].

At this point, if a randomized mixture (via Process B or B*) is supplemented by additional 50:50 material in an amount equal to the amount of the purified product that was isolated from the preceding crystallization, an equal amount of purified product (100% yield, based on the alkyl casylate used to prepare the supplement) is theoretically available from the crystallization stage of the recycle process.

Process C: Recycling of the casylate auxiliary. In this process an alkyl casylate is recovered from a quaternary salt or metal casylate salt, and may be reused in Process A, presented above. To a strongly stirred solution or slurry of thoroughly dried metal or quaternary casylate salt in an inert solvent, such as a chlorinated hydrocarbon, preferably 1,2-dichloroethane, is carefully added a slight molar excess of concentrated sulfuric acid, followed by 1.1 or more equivalents of triethyl or trimethyl phosphite. Other trialkyl phosphites may be used. After the trialkyl phosphite addition (slight exotherm), the stirred mixture is heated to 80°–100° C. for one hour, or until analysis, such as by NMR, shows that alkyl casylate is the only casylate species present. If the crude reaction mixture is liquid, as is the case with lithium and quaternary ammonium compounds, it is stripped of all volatile components at reduced pressure, and the residue is taken up in a mixture of ether and water. The water layer is extracted with ether, and the combined ether portions are washed (water), dried, and stripped of solvent to afford the alkyl casylate in high yield. If the crude reaction mixture is semi-solid, as is the case with sodium and potassium compounds, water is added (solids dissolve) and the layers are separated. The water layer is extracted with the reaction solvent (preferably 1,2-dichloroethane), and the combined organic portions are washed (water), dried, and stripped of solvent to afford the alkyl casylate in high yield.

Figure 5:
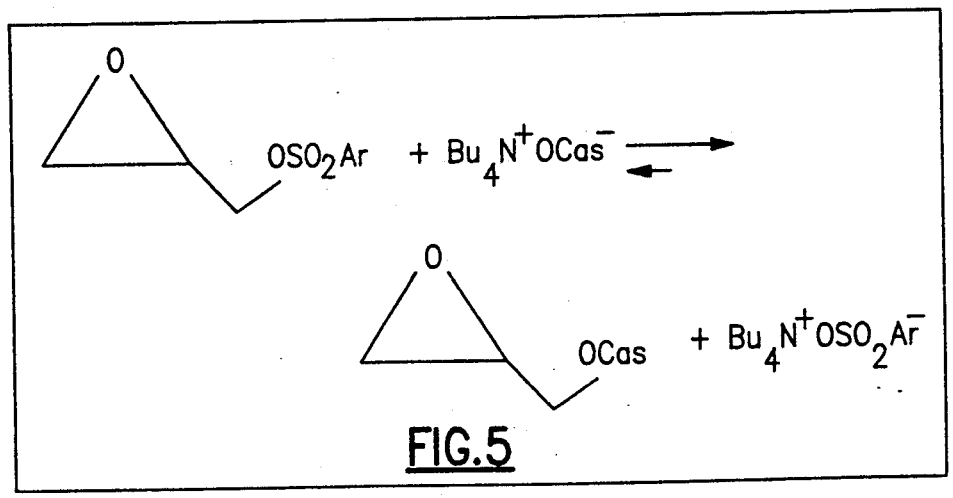

Process D: In an alternative embodiment of the invention, crude glycidyl casylate can be prepared from other starting materials by the reaction in accordance with FIG. 5. An excess of racemic or enantiomerically enriched glycidyl sulfonate, such as glycidyl tosylate, and a quaternary casylate, such as tetrabutylammonium casylate, are heated together and the reaction monitored, preferably by $^1$H NMR, until the reaction no longer is proceeding forward appreciably. The forward reaction products are favored at equilibrium. The resulting products are crude glycidyl casylate and Bu$_4$N$^+$OSO$_2$Ar$^-$.

The reaction mixture then is dissolved in a minimum of an appropriate solvent, preferably diethyl ether, ethyl acetate, methyl ethyl ketone, or some mixture thereof, and tetrabutylammonium salts are precipitated out, by cooling if necessary. The filtrate is stripped of solvent, and dissolved in acetone, or another suitable solvent, and cooled to 10° C. In the event that there are unreacted arenesulfonates remaining, a solution of lithium bromide in acetone, or other suitable solvent, is added, and the mixture monitored by $^1$H NMR or TLC until glycidyl arenesulfonate no longer is detected. Lithium bromide selectively reacts with glycidyl arenesulfonate. Glycidyl casylate and epibromohydrin may then be isolated and recovered by methods well known to the art. This method of casylate preparation does not allow the substitution of racemic epibromohydrin for glycidyl arenesulfonate. Stoichiometric casylate ion as part of either a quaternary or metal salt does not displace covalent bromides to any useful extent. Because 88–90% optically pure glycidyl p-toluenesulfonates and 3-nitrobenzenesulfonates (either enantiomer) are commercially available, this method does provide a convenient route to either of the low-melting stereoisomers of formula (5) in 88–90% optical purity.

Although process D was explained with reference to glycidyl arenesulfonate, it is applicable to any arenesulfonate analog of any casylate which undergoes Process B, described above, by reacting that arenesulfonate analog with a quaternary casylate.

Figure 6:
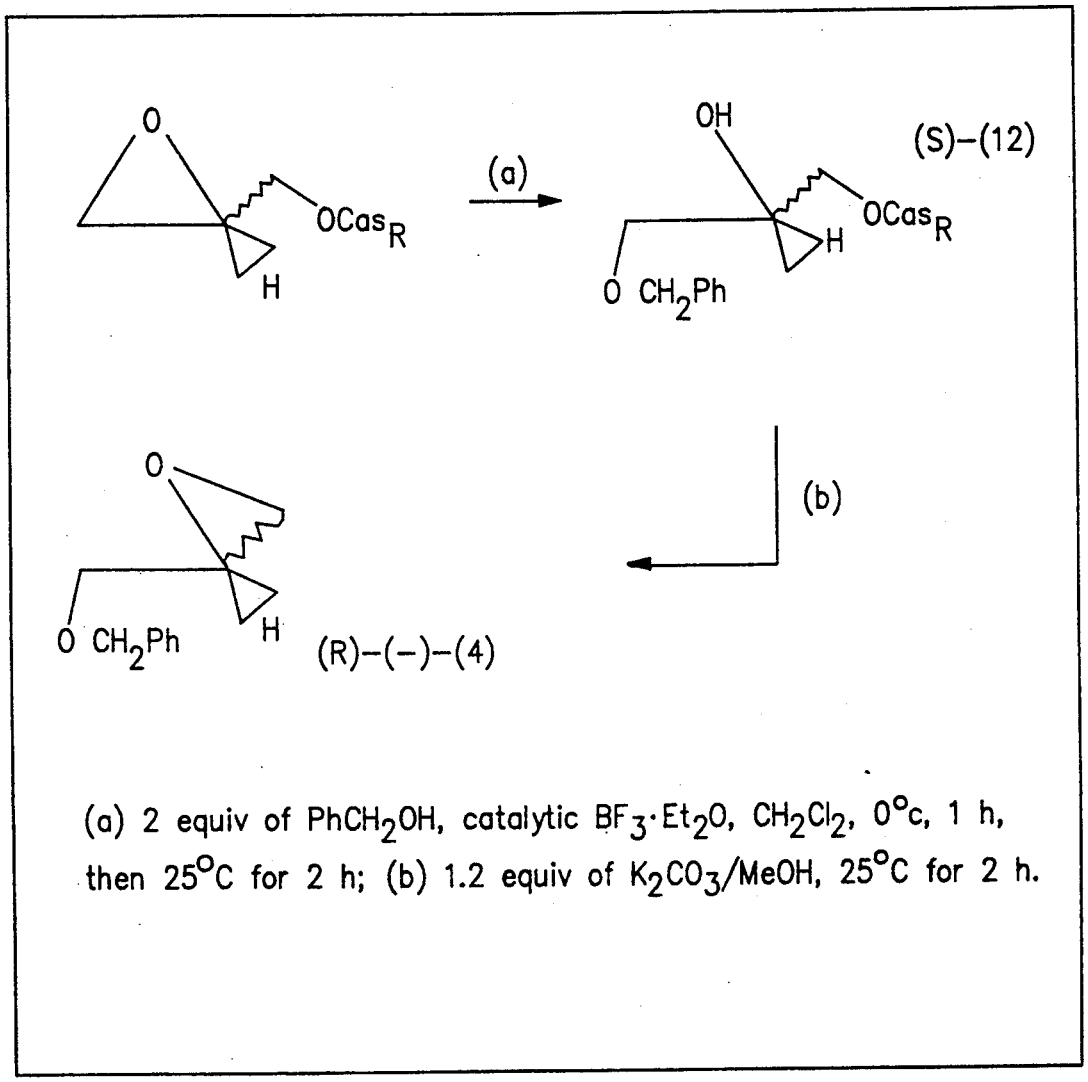

An Application of glycidyl camphorsulfonate in Asymmetric Synthesis: Referring now to FIG. 6, there is shown a conventional reaction scheme in which is utilized as a starting material a stereoisomer of the novel compound of formula (5) in a 98+% isomerically pure form. At the present time, the inventor has obtained product consisting of 98+% optically pure benzyl glycidyl ether in at least 70% overall yield. Thus Epi,OCas, is converted to (S)-(12), which is assayed directly by $^1$H NMR spectroscopy to be 98+% pure (no isomer detected). Conversion of (S)-(12), to (R)-(−)-(4) again affords 98+% optically pure material, as indicated by chiral shift reagent analysis ($^1$H NMR; no isomer detected) and optical rotation $[\alpha]_D -10.8°$ (c 5, MeOH).

While this invention has been explained with reference to the structure disclosed herein, it is not confined to the details set forth and this application is intended to cover any modifications and changes as may come within the scope of the following claims:

What is claimed is:

1. A casylate of formula (11), wherein $R_1$, $R_2$, and $R_3$ are bromide, bromomethyl, ethyl, methyl, or hydrogen, provided that $R_1$, $R_2$, and $R_3$ are each different, or formulas (12) or (13), wherein $R_1$, $R_2$, and $R_3$ independently of one another are bromomethyl, ethyl, methyl, or hydrogen, n is 0, 1, or 2, and Y is oxygen, C=O, or —CH$_2$—, produced by the steps of

(11)

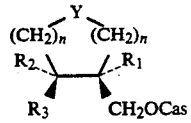
(12)

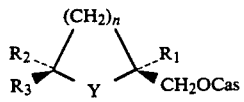
(13)

reacting at least 1.0 equivalents of a racemic or achiral bromide analog thereof, with an alkyl casylate in the presence of a quaternary salt catalyst at a temperature of about 115° to 125° C. to yield a mixture; and thereafter distilling away excess of said bromide from said mixture.

2. A glycidyl casylate of formula (8a) or (8b) produced by the steps of reacting about 1.5 to 3.0 equivalents of a racemic of achiral bromide analog thereof, wherein $R_1$, $R_2$, and $R_3$ independently of one another are

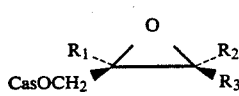
(8a)

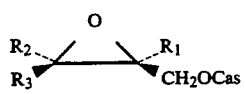
(8b)

bromomethyl, ethyl, methyl, or hydrogen, with about 1.0 equivalents of an alkyl casylate in the presence of a quaternary salt catalyst at a temperature of about 115° to 125° C. to yield a mixture; and thereafter distilling away an excess of said bromide analog from said mixture under reduced pressure.

3. A stereoisomer of a glycidyl casylate of formula (8a) or (8b), wherein $R_1$, $R_2$, and $R_3$ are each hydrogen, and said glycidyl casylate has an isomeric purity exceeding 98%, produced by the steps of reacting about 1.5 to 3.0 equivalents of a racemic

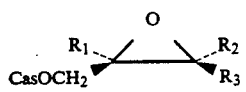
(8a)

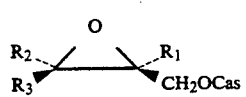
(8b)

or achiral bromide analog thereof, wherein $R_1$, $R_2$, and $R_3$ independently of one another are bromomethyl, ethyl, methyl, or hydrogen, with about 1.0 equivalents of an alkyl casylate in the presence of a salt catalyst selected from the group of a quaternary ammonium casylate salt and a quaternary ammonium bromide salt at a temperature of about 115° to 125° C. to yield a mixture; and thereafter distilling away an excess of said bromide analog from said mixture under reduced pressure.

4. A casylate of formula (8a) or (8b), wherein $R_1$, $R_2$, and $R_3$ are each hydrogen,

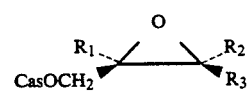
(8a)

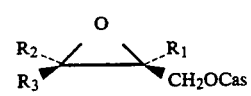
(8b)

produced by the step of reacting a racemic or enantiomerically enriched arenesulfonate analog thereof with a quaternary ammonium casylate to yield a result.

5. A stereoisomer of glycidyl casylate having an isomeric purity exceeding 98%, of the formula 5(a) or 5(b) or 5(c) or 5(d)

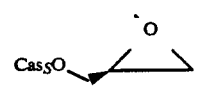
(5a)

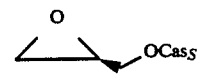
(5b)

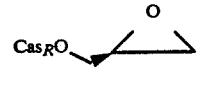
(5c)

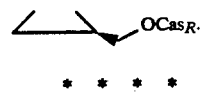
(5d)

* * * * *